Figure 1:
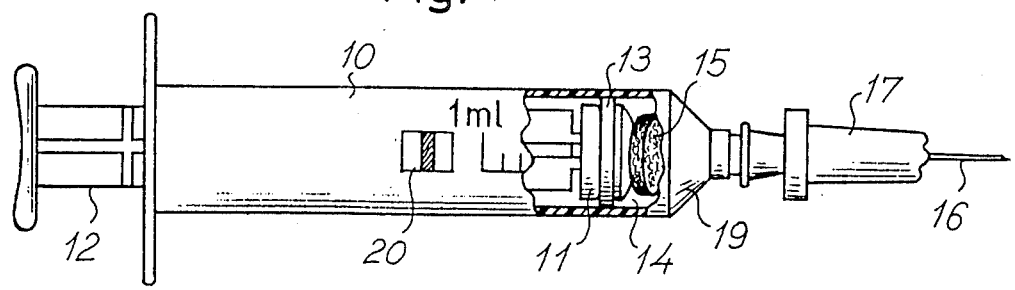

United States Patent [19]

Eisenhardt et al.

[11] Patent Number: 4,687,000

[45] Date of Patent: Aug. 18, 1987

[54] COMPOSITION AND SAMPLING RECEPTACLE METHOD FOR TREATING BLOOD WITH ANTICOAGULANT

[75] Inventors: Anne R. Eisenhardt, Birkerod; Ole M. Hansen, Copenhagen, both of Denmark

[73] Assignee: Radiometer A/S, Copenhagen, Denmark

[21] Appl. No.: 713,911

[22] PCT Filed: Jul. 13, 1984

[86] PCT No.: PCT/DK84/00069

§ 371 Date: Mar. 15, 1985

§ 102(e) Date: Mar. 15, 1985

[87] PCT Pub. No.: WO85/00662

PCT Pub. Date: Feb. 14, 1985

[30] Foreign Application Priority Data

Jul. 15, 1983 [DK] Denmark ............................. 3261/83
Jun. 12, 1984 [DK] Denmark ............................. 2861/84

[51] Int. Cl.⁴ .............................................. A61B 5/00
[52] U.S. Cl. ..................................... 128/760; 128/763
[58] Field of Search ............... 128/760, 763; 604/269, 604/416

[56] References Cited

U.S. PATENT DOCUMENTS 4,252,118 2/1981 Richard et al. ..................... 604/110
4,479,799 10/1984 Thiel ................................... 128/763
4,571,382 2/1986 Adachi ................................. 435/7

Primary Examiner—Kyle L. Howell
Assistant Examiner—Randy Citrin

Attorney, Agent, or Firm—Stiefel, Gross, Kurland & Pavane

[57] ABSTRACT

In order to counteract coagulation of a blood sample which is collected from an animal or a human body (24) and introduced into a receptacle, such as a syringe chamber (14), an anticoagulant is added to the sample within the receptacle. The anticoagulant may be capable of binding cation species in the blood, which are subsequently to be measured. Such cation species comprise hydrogen ions, ammonium ions, alkaline metal ions such as potassium and sodium ions, and alkaline earth metal ions such as magnesium and calcium ions. In order to compensate for the proportions of selected cation species which are bound by the anticoagulant, an additive containing such cation species is added to the blood sample so as to obtain substantially the same concentration of the selected cation species in an unbound condition in the anticoagulant treated blood sample as in the untreated blood sample.

The anticoagulant and the additive are preferably added to the blood sample as a composition which may be deposited on or carried by a carrier body (15) which may be arranged within the receptacle in which the blood sample is introduced. The bulk density of the nonwetted carrier body is preferably smaller than the specific weight of the blood sample so as to avoid trapping of air bubbles within the receptacle. In its wetted condition the bulk density of the carrier body is preferably also different from the specific weight of the blood sample so that the carrier body (15) may be used as an agitating member improving mixing of the anticoagulant composition with the blood sample. The carrier body (15) may, for example, be made of filtering paper.

24 Claims, 3 Drawing Figures

U.S. Patent    Aug. 18, 1987    4,687,000

COMPOSITION AND SAMPLING RECEPTACLE METHOD FOR TREATING BLOOD WITH ANTICOAGULANT

The present invention relates to a method of treating a blood sample with an anticoagulant.

In connection with the analysis of whole blood it is known to employ sampling equipment containing anticoagulant in a dry or liquid form for the prevention of coagulation of the sample.

In Hill, A. B. et al., *Anesthesiology*, September 1979, p. S207, it is disclosed that the use of heparin as anticoagulant in blood samples reduces the potentiometrically determined electrolyte values in the sample, because the heparin is capable of binding a certain amount of the electrolyte.

Radiometer A/S, Copenhagen, has previously developed and marketed liquid anticoagulant compositions for use in connection with blood sampling syringes and sampling equipment in the form of capillary tubes containing a coating on the tube inner wall of a dry anticoagulant composition wherein the anticoagulant composition is especially adapted for use in connection with the sampling of blood which is to be subsequently analysed for the content of ionized calcium. These anticoagulant compositions comprise sodium heparinate, an adjusted amount of calcium chloride and, if desired, water.

The calcium chloride content is adjusted such that the amount of ionized calcium which is bound by the heparinate when brought in contact with the blood sample is provided by the calcium chloride present in the anticoagulant composition. Thereby the resulting content of ionized calcium in the blood sample will be essentially the same as the original content irrespective of the addition of calcium binding heparinate.

The present invention is based on the finding that it is possible to compensate for the anticoagulant binding of several cation species so that the contents of said cation species in one and the same blood sample may be determined by a subsequent analysis without any substantial errors.

Thus, the present invention provides a method for treating a blood sample with an anticoagulant, said method comprising:
passing a predetermined volume of a sample of whole blood into a receptacle,
adding to the blood sample within the receptacle a predetermined amount of the anticoagulant, which is capable of binding different cation species in the blood, and
adding to the blood sample within the receptacle an additive including selected ones of said different cation species in amounts compensating for proportions of the selected cation species bound by the anticoagulant so as to obtain substantially the same concentration of the selected cation species in an unbound condition in the anticoagulant treated blood sample as in the untreated blood sample.

The compensation for the proportions of the selected cation species bound by the anticoagulant is preferably so that the relative error caused by the binding to the anticoagulant is less than or equal to 0.5 percent, in particular less than or equal to 0.35 percent.

The provision of such a universal method of treating a blood sample with an anticoagulant is a significant advance. The user thereby avoids having to work with various treatment methods and/or sampling equipment and/or anticoagulants depending on which subsequent potentiometric analysis is to be carried out, which, among other things, has the advantage of eliminating the otherwise clear risk of mistake. In other words, by employing the method according to the invention it is possible to attain correct analytical results for different components by means of a single blood sample. This is not only of importance from the point of view of saving time and reducing the consumption of materials but also from the point of view of the patient, as the number of blood sample withdrawals is reduced. Moreover, many analytical instruments are adapted to analyse the blood sample with respect to particular combinations of cations or electrolytes, and the present invention makes it possible to provide blood sampling receptacles and anticoagulant compositions dedicated to such combinations.

The amount of anticoagulant used should on the one hand ensure the blood sample against coagulation, but should on the other hand be as small as possible in order to minimize the interference with the blood sample. The selected cation species are preferably selected from the group consisting of hydrogen ions, ammonium ions, alkaline metal ions such as lithium, potassium and sodium ions, and alkaline earth metal ions such as magnesium and calcium ions.

The amount of anticoagulant employed should preferably be such that the amount of a cation species that is removed by the binding caused by the anticoagulant is a minor proportion of the original amount of the cation species such as less than 10 percent, in particular less than 5 percent, and especially less than 2 percent of the original amount.

The anticoagulant used in the method of the invention is preferably heparin or a heparin derivative such as a heparin salt.

The receptacle used in the method of the invention may be of the capillary tube type, the syringe type or the vacuum container type.

The final heparin concentration in the blood sample should be in the range of 8-150 interantional units/ml (IU/ml) depending on, among other things, the sampling technique and the equipment used. Since it is preferred to use the smallest possible amount of heparin it is preferred that the final concentration in the blood sample is 20-80 IU/ml, such as 50 IU/ml.

If a receptacle of the capillary tube type is employed, an amount of heparin resulting in a concentration of 40-100 IU/ml, in particular about 50-80 IU/ml, is generally considered suitable.

The additive may comprise the selected cation species as e.g. salts thereof or as part of other compounds that will release the ions in question when brought into contact with the blood sample.

In one embodiment of the method according to the invention at least part of the additive is added together with the anticoagulant as an anticoagulant composition.

In a preferred embodiment of the method according to the invention at least part of the additive forms a compound with the anticoagulant. An example of such a compound is a heparin salt.

The anticoagulant used in the method according to the invention may also contain an inactive cation. The anticoagulant may also contain a compound of the anticoagulant with an inactive cation in order to provide the sample with sufficient anticoagulant without introducing undesired amounts of the ions to be analyzed.

In a preferred embodiment of the invention the part of the additive forming a compound with the anticoagulant is selected from the group consisting of sodium heparinate and potassium heparinate. The use of such compounds will make it possible to perform analysis of the content of both $Na^+$ and $K^+$, both ions being bound by heparin-based anticoagulants. The presence of the inactive cation lithium within the anticoagulant composition is preferred in order to provide the sample with sufficient heparinate.

By using adjusted amounts of lithium heparinate, sodium heparinate and potassium heparinate it is possible to avoid adding unnecessary anions to the blood sample.

In another preferred embodiment of the method of the invention the anticoagulant composition comprises a mixture of lithium heparinate and sodium heparinate in a ratio of between 65:35 and 35:65, preferably 50:50 (determined as international units—IU) as well as a potassium salt.

If the content in the blood sample of e.g. $Na^+$, $K^+$ and $Ca^{++}$ is to be determined in the subsequent analysis and the anticoagulant composition is a composition based on heparin, the composition may comprise a heparin salt of an inactive cation, in particular lithium, as well as salts of potassium, sodium and calcium. Such salts may be chlorides, heparinates, mixtures thereof etc. and in adjusted amounts. These ions are the ions most frequently analysed in potentiometrical analysis of blood.

Thus, it is now possible to provide a universally applicable anticoagulant composition that may be used irrespective of which cation species within the group of clinically interesting cations capable of being bound by anticoagulant are to be determined in a subsequent analysis. It is possible to prepare anticoagulant compositions to be housed within a receptacle and to be used in connection with blood samples that are subsequently to be analysed for such components as $Na^+$, $K^+$, $Ca^{++}$, $Mg^{++}$ and $H^+$ and any combination thereof. Compositions adapted for more or fewer components are of course possible.

In the method of the invention the anticoagulant composition may be present in a liquid form and with such a content of the cation species to be determined that both the analytical error caused by the anticoagulant binding and the analytical error caused by the dilution are compensated.

If a liquid anticoagulant solution is added to the blood sample in an amount of up to 1-10 percent of the volume of the blood sample it is obvious that analytical results expressing a concentration or an activity will be erroneous to a considerable extent unless the anticoagulant composition is adjusted according to the composition of the blood sample.

It is therefore preferred that a liquid anticoagulant composition used in the method of the invention, apart from containing the necessary amount of the selected cation species in an amount sufficient to eliminate the error caused by a anticoagulant binding, also contains the selected cation species in a concentration corresponding to the concentration in normal blood, whereby the error caused by dilution is essentially eliminated.

In another embodiment of the method of the invention, the anticoagulant composition is added as a solid.

In a preferred embodiment of the method according to the invention, at least part of the anticoagulant and/or at least part of the additive is carried by a carrier body which is introduced into the receptacle, the receptacle preferably being of the syringe type or of the vacuum container type. Thus, the carrier body may contain a predetermined amount of anticoagulant and/or additive and in that case two or more carrier bodies are introduced into the receptacle. In the preferred embodiment, however, each carrier body contains the necessary amount of anticoagulant as well as of additive, so that only one carrier body should be introduced into the receptacle for receiving the blood sample.

The carrier body is preferably of such a type that trapping of air bubbles within the carrier body or the receptacle is avoided. Therefore, the bulk density of the non-wetted carrier body is preferably smaller than the specific weight of the blood sample, so that during at least the initial part of the sampling procedure the carrier body is floating on the surface of the blood sample being introduced into the receptacle, whereby trapping of air bubbles between the outer surface of the carrier body and the adjacent inner surface of the receptacle is avoided. The carrier body may be made from a solid material or may have one or more inner cavities, which are separated from the outer surface of the carrier body by walls which are impermeable to air and liquid. In that case the anticoagulant and/or the additive may be arranged on the outer surface of the carrier body.

In the preferred embodiment, however, the carrier body comprises a porous or fibrous material, which may contain or be impregnated with the anticoagulant and/or the additive. Such a porous or fibrous material may float on the blood sample until the blood penetrates into the porous or fibrous material and wets the carrier body, and the bulk density of the wetted carrier body may exceed the specific weight of the blood. The carrier body may, for example, comprise cellulose material such as filtering paper, synthetic fibres, glass fibres, mineral fibres or the like. The carrier body may be shaped in any suitable manner, for example as a ball, a disc, a cylinder, a cone, a strip, or a sheet, and the contour of the body may, for example, be circular, eliptical, polygonal, etc.

The material of the carrier body on which the anticoagulant and/or the additive is arranged should preferably be substantially inactive so as not to react with and influence on the cation species or other components of the blood sample to be measured. Therefore, in case of blood electrolyte analysis it is important that the ash content of the carrier body material is low.

In order to determine the necessary content of a specific cation species in the anticoagulant composition it is necessary to provide information concerning to what extent the cation species in question is bound by the anticoagulant or the anticoagulant composition.

The determination of the necessary amount of the cation/cations in question may be carried out theoretically based on the knowledge of the equilibrium constant, but it is considered easier to determine the amount in question in the following way: a sample with a content of a cation corresponding to the content in normal blood is used. To the sample is added anticoagulant to provide the anticoagulant concentration desired in the sampling equipment. Thereafter titration is performed with a solution of a known content of a cation, while the cation content in the sample is monitored potentiometrically. When the monitored content reaches the initial value (the normal value for blood) the amount of the cation necessary to compensate for the binding of the cation by the anticoagulant has been determined.

Based on experiments it has been found that the binding of $Na^+$ and $K^{30}$ in aqueous solutions containing 80 IU/ml heparin is $K^+$: −0.049 mmol/l
$Na^+$: −1.35 mmol/l.

For whole blood the effect is approximately the double of the above, which may be ascribed to the fact that the hematocrit value is approximately 0.5.

If the anticoagulant composition incorporates a compound between the anticoagulant and one of the cation species to be determined it is likewise necessary to know the amount of the cation species in question present in the compound. Thus, it may be calculated that 80 IU/ml sodium heparinate in aqueous solutions will rise to a $Na^+$-content of approximately 2.47 mmol/l provided that the entire amount of $Na^+$ is liberated.

The invention also provides a blood sampling receptacle adapted to define a blood receiving space therein and comprising:
  blood inlet means for introducing a sample of whole blood into the blood receiving space of the receptacle,
  an anticoagulant arranged within said space and being capable of binding different cation species in the blood, and
  an additive arranged within said space and including selected ones of different cation species in amounts compensating for proportions of the cation species bound by the coagulant when the blood receiving space has been substantially filled with blood, so as to obtain substantially the same concentration of said selected cation species in an unbound condition in the blood which has been introduced into the blood receiving space, as in the blood prior to being introduced into said space.

According to a further aspect the present invention also provides an anticoagulant composition to be added to a sample of whole blood of a predetermined volume housed within a receptacle so as to prepare the blood sample for analysis, said composition comprising:
  an anticoagulant which is capable of binding different cation species in the blood, and
  an additive including selected ones of said different cation species in amounts compensating for proportions of the selected cation species which may be bound by the anticoagulant so as to obtain substantially the same concentration for the selected cation species in an unbound condition in the blood sample after as prior to the addition of the anticoagulant composition.

The invention is further illustrated by the following non-limiting examples.

EXAMPLE 1

Blood sampling receptacles adapted for withdrawing a blood sample for subsequent analysis of the content in the sample of $Na^+$ and $K^+$ are prepared. The blood sampling receptacles prepared are shaped as capillary tubes treated with dry anticoagulant composition. Capillary tubes are prepared in two sizes, i.e. 130 μl and 165 μl, both types having a diameter of 1.6 mm.

The 130 μl tubes are treated with a dry anticoagulant composition in the form of a heparin composition prepared as specified below. The tubes contain heparin in an amount corresponding to a final concentration in the blood sample of 50 IU/ml.

The 165 μl tubes are treated with a similar heparin composition, also specified in details below. These tubes contain heparin in an amount corresponding to a final concentration in the blood sample of 80 IU/ml.

The treatment of the capillary tubes with heparin is carried out by a special process, in which a heparin solution with an adjusted content of $Na^+$ and $K^+$ is used. A drop of the solution is blown through each individual tube with simultaneous drying resulting in a largely evenly distributed film of dry heparin composition on the inside wall of the tubes.

The two heparin solutions for preparing the 130 μl, 50 IU/ml capillary tubes (solution I) and 165 μl, 80 IU/ml capillary tubes (solution II), respectively, were prepared as follows:

Solution I

Initially a stock solution is prepared with the following composition:

| | |
|---|---|
| Sodium heparin | 500,000 IU |
| Lithium heparin | 500,000 IU |
| Deionized water (Conductivity <0.5 μS) up to | 500 ml. |

Sodium heparin and lithium heparin are available from Lövens Kemiske Fabrik, Copenhagen, with the following specifications:

| | |
|---|---|
| Sodium heparin: | 160–180 IU/mg |
| | 10.3–11.2% Na (w/w) |
| | <0.3% K (w/w) |
| Lithium heparin | 160–180 IU/mg |
| | 3.4–3.8% Li (w/w) |
| | <0.1% K (w/w) |

The content of sodium and potassium in the stock solution is determined in a flame photometer of the type FLM3 from Radiometer A/S, Copenhagen.

The resulting solution should have a sodium content in the interval 26 mmol/l—Na determined ≦29 mmol/l. If the content is outside these limits it is adjusted by adding either NaCl (analytical purity) or lithium heparinate solution.

The content of potassium in the resulting solution is also determined by means of flame photometry. The potassium content should be in the interval of 0.9 mmol/l ≦ K determined ≦ 1.30 mmol/l. If the potassium content is higher the liquid is discarded, and if the potassium content is lower the content is adjusted by adding KCl in the form of a solution of a 0.5M KCl solution (purity of KCl is analytical).

Solution II

First a stock is prepared with the following composition:

| | |
|---|---|
| Sodium heparin | 750,000 IU |
| Lithium heparin | 750,000 IU |
| Deionized water (Conductivity <0.5 μS) up to | 500 ml. |

The same chemicals as listed in connection with solution I are used.

The content of the stock solution of sodium and potassium is determined on a flame photometer of the type FLM3 from Radiometer A/S, Copenhagen.

The resulting solution should have a sodium content in the interval 38 mmol/l ≦ Na determined ≦ 44 mmol/l. If the content is outside these limits it is adjusted by means of adding either NaCl solution or lithium heparinate solution.

The content of potassium in the resulting solutions is also determined by means of flame photometry. The potassium content should be in the interval 1.7 mmol/l ≦ K determined ≦ 2.0 mmol/l. If the potassium content is higher the liquid is discarded, and if the potassium content is lower the content is adjusted by means of adding KCl as a 0.5M KCl solution.

Comparison tests are carried out with the above prepared 130 μl, 50 IU/ml and 165 μl, 80 IU/ml tubes and non-treated capillary tubes. An aqueous $Na^+/K^+$ solution as well as blood is used as a sample. The aqueous $Na^+/K^+$ solution contains 152 mmol/l $Na^+$ and 4 mmol/l $K^+$, and the blood is human blood.

The content of $Na^+$ and $K^+$ in the samples are determined on an automatic analytical instrument of the type KNA1 from Radiometer A/S, Copenhagen. The two components are in this instrument determined by means of ion selective measuring electrodes.

The following results are obtained:

| 130 μl, 50 IU/ml Capillary Tubes: | | | |
|---|---|---|---|
| | Untreated Tubes | Treated Tubes | Δ mmol/l |
| Aqueous solution | | | |
| $K^+$ mmol/l | 3.858 | 3.860 | 0.002 |
| $Na^+$ mmol/l | 146.58 | 146.82 | 0.24 |
| Blood | | | |
| $K^+$ mmol/l | 4.022 | 4.027 | 0.005 |
| | 3.238 | 3.244 | 0.006 |
| $Na^+$ mmol/l | 140.20 | 140.65 | 0.45 |
| | 138.97 | 139.45 | 0.48 |

| 165 μl, 80 IU/ml, Capillary Tubes: | | | |
|---|---|---|---|
| | Untreated Tubes | Treated Tubes | Δ mmol/l |
| Aqueous solution | | | |
| $K^+$ mmol/l | 3.862 | 3.867 | 0.005 |
| $Na^+$ mmol/l | 146.81 | 147.25 | 0.44 |
| Blood | | | |
| $K^+$ mmol/l | 3.848 | 3.846 | −0.002 |
| | 3.918 | 3.920 | 0.002 |
| | 3.180 | 3.212 | 0.032 |
| $Na^+$ mmol/l | 143.45 | 143.95 | 0.50 |
| | 141.53 | 141.95 | 0.42 |
| | 139.03 | 139.42 | 0.39 |

EXAMPLE 2

PREPARATION OF BLOOD SAMPLING EQUIPMENT

A. Preparation of anticoagulant-carrying body

On a laboratory scale the following procedure is used:

Discs of filtering paper of the type Whatman A-A with a diameter of 6 mm and a thickness of 0.85 mm are used. These discs are capable of absorbing approximately 25 μl liquid.

By means of a pipette 20 μl of an aqueous solution with the following composition is transferred to the discs

| Lithium heparinate | 1750 IU/ml |
|---|---|
| Sodium heparinate | 1750 IU/ml |
| $CaCl_2$, 2 $H_2O$ | 0.60 g/l |
| KCl | 0.08 g/l |
| The remainder | Water |

The discs are then dried by means of hot air at a temperature of about 80° C.

The dried discs contain 70 IU heparinate, which is compensated for the binding to the heparinate of $Na^+$, $K^+$ and $Ca^{++}$.

Since by using heparinate of varying origin a certain variation in the cation-binding capacity of heparinate may occur it should be checked that the solution composed as listed above actually does give the desired compensation.

B. Mounting of the Equipment

Each of the above heparin-treated discs is placed in the cylinder of a ventilated 1 ml artery syringe of the type B109 from Radiometer A/S, Copenhagen. The syringe piston is inserted into the cyliner, and the syringe is packaged and sterilized by means of ethylene oxide.

Figure 2:
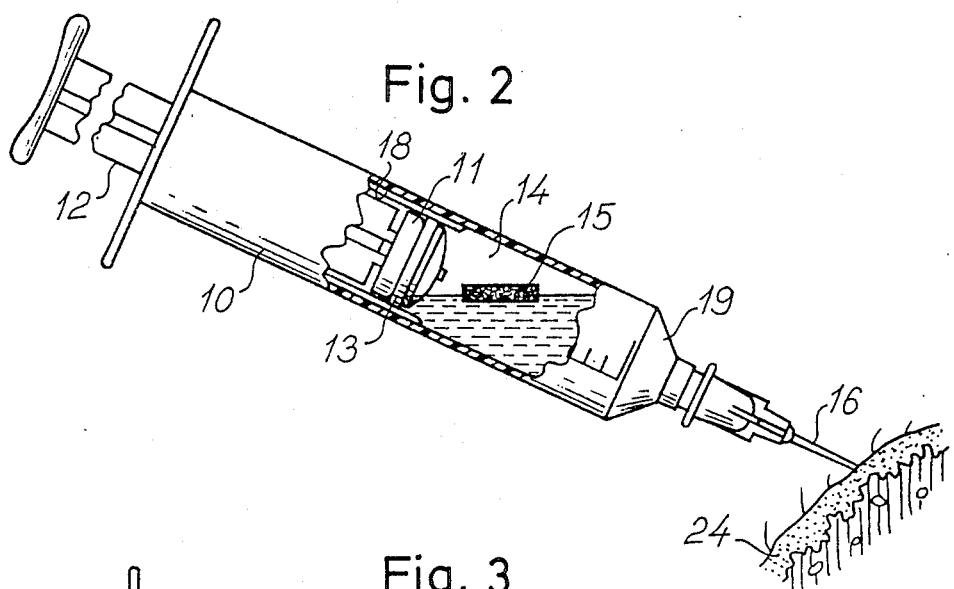
Figure 3:
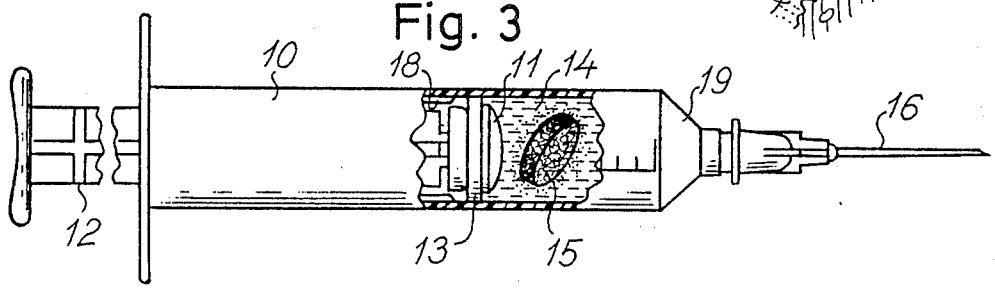

The invention will now be further described with reference to the drawings, wherein FIG. 1 is a side view and partially sectional view of a blood sampling syringe which is an embodiment of the sampling receptacle according to the invention, FIG. 2 is a side view and partially sectional view of the syringe shown in FIG. 1, while a blood sample is being collected, FIG. 3 is a side view and partially sectional view of the syringe shown in FIGS. 1 and 2 after the collection of the blood sample.

The syringe shown in FIGS. 1–3 comprises a syringe cylinder or barrel 10 and a piston 11 displaceably arranged within the cylinder 10 and connected to a piston rod 12. A resilient sealing ring 13 mounted on the piston 11 is in sealing engagement with the surface of the cylinder or barrel 10 so that the piston 11 defines a syringe chamber 14 at the inner end of the cylinder 10, and this chamber contains a disc-like carrier body 15, which contains an anticoagulant composition as described in more detail below. A hollow needle 16 is mounted on and extends from one end of the cylinder 10, and the inner space of the hollow needle 16 communicates with the syringe chamber 14. Before use of the syringe the hollow needle 16 may be covered by a protective cap 17, as shown in FIG. 1, where the free end of the cap has been cut away.

Axially extending fins or ribs 18 are formed on the inner surface of the cylinder 10 at a position spaced substantially from an end wall 19 of the cylinder adjacent to the needle 16.

When the syringe shown in FIG. 1 is to be used for collecting a sample of arterial blood, the piston rod 12 and the piston 11 connected thereto are moved outwardly till the piston 11 reaches a position in which the sealing ring 13 comes into engagement with the fins or ribs 18, whereby the sealing engagement of the ring is disturbed so that the syringe chamber 14 is vented to the atmosphere. The cylinder or barrel 10 may be made from a transparent material and may be provided with a marking 20 indicating the position of the piston 11 establishing communication between the atmosphere and the syringe chamber 14. When the piston has been moved to its venting position the protective cap 17 is removed, and the free pointed end of the hollow needle may be inserted into an artery in a human or animal body 24 as indicted in FIG. 2. Arterial blood may then flow into the vented syringe chamber 14 under the arterial blood pressure, and the carrier body 15, which in its non-wetted condition preferably has a bulk density which is smaller than the specific weight of the blood, will then float, at least during the intial part of the sampling procedure, on the surface of the blood flowing into the syringe chamber 14 as illustrated in FIG. 2.

When the syringe chamber 14 has been completely filled with blood the needle 16 is removed from the artery, and the piston rod 12 and the piston 11 are pushed slightly inwardly so as to disengage the sealing ring 13 from the ribs 18 and reestablish sealing engagement between the sealing ring 13 and the adjacent inner wall part of the cylinder 15. The pores or interstices of the fibrous or porous carrier body 15 eventually become filled with blood and the body thereby obtains a bulk density exceeding the specific weight of the blood. This situation is illustrated in FIG. 3 in which the syringe chamber 14 contains the carrier body 15 and a blood sample free of air and is sealed from the ambient atmosphere.

The carrier body 15 may, for example, be a disc of filtering paper prepared as described in Example 2. Because the bulk density of the wetted carrier body 15 is different from the specific weight of the blood, the carrier body may function as an agitating member mixing the anticoagulant composition of the carrier body with the blood sample within the syringe chamber 14, when a reciprocating, rotating or other suitable movement is imparted to the syringe. When the anticoagulant composition has been dissolved in and mixed with the blood sample, the blood sample thus prepared may be injected into a blood analyser.

It should be understood that the carrier body 15 need not carry an anticoagulant as well as an additive compensating for the cation species being bound by the coagulant. Thus, the carrier body may carry either the anticoagulant or the additive or part thereof. As an example, the anticoagulant may be applied to an inner wall part of the syringe chamber 14 and the additive may then be carried by the carrier body, or vice versa. It is also possible to introduce two or more carrier bodies into the syringe chamber 14, and one of the carrier bodies may then carry the anticoagulant while the additive or part thereof is carried by another carrier body.

We claim:

1. A blood sampling device comprising receptacle means defining a blood receiving space therein for receiving a blood sample, said means including
   a blood inlet means for introducing a sample of whole blood into the blood receiving space,
   an anticoagulant present within said space, the anticoagulant being an anticoagulant capable of binding cation ion species in blood, and
   an additive present within said space and including several selected cation species which occur in blood, each species in the additive being present in an amount substantially corresponding to the binding capacity for that species that the anticoagulant exhibits when in equilibrium with a blood sample of substantially the same volume as that of said receptacle so as to ensure substantially the same concentration of each of the selected cation species in an unbound condition in the blood after the blood has been introduced into the blood receiving space as is in the blood prior to being introduced into said space.

2. A blood sampling device according to claim 1 wherein the anticoagulant, the additive, or the anticoagulant and the additive are carried by a carrier body.

3. A blood sampling device according to claim 2 wherein the bulk density of the carrier body in a non-wetted state is less than the specific weight of the blood sample.

4. A blood sampling device according to claim 3 wherein the carrier body comprises a porous or fibrous material.

5. A blood sampling device according to claim 4 wherein the carrier body comprises cellulose material.

6. A blood sampling device according to claim 5 wherein the carrier body comprises filtering paper.

7. A blood sampling device according to claim 2 wherein the carrier body has a disc-like shape.

8. A blood sampling device according to claim 1 wherein said selected cation species are selected from the group consisting of hydrogen ions, ammonium ions, alkali metal ions, and alkaline earth metal ions.

9. A blood sampling device according to claim 8 wherein said selected cation species comprise alkali metal ions selected from the group consisting of potassium and sodium ions.

10. A blood sampling device according to claim 8 wherein said selected cation species comprise alkaline earth metal ions selected from the group consisting of magnesium and calcium ions.

11. A blood sampling device according to claim 1 wherein the anticoagulant is selected from the group consisting of heparin and heparin derivatives.

12. A blood sampling device according to claim 11 wherein heparin is present in an amount of from 40 to 100 IU/ml of the blood receiving space.

13. A blood sampling device according to claim 12 wherein heparin is present in an amount of from 50 to 80 IU/ml of the blood receiving space.

14. A blood sampling device according to claim 1 wherein at least part of the additive is combined with the anticoagulant into an anticoagulant composition.

15. A blood sampling device according to claim 10 wherein at least part of the additive forms a compound with the anticoagulant.

16. A blood sampling device according to claim 15 wherein said compound is a heparin salt.

17. A blood sampling device according to claim 15 wherein said compound is selected from the group consisting of lithium heparinate, sodium heparinate, and potassium heparinate.

18. A blood sampling device according to claim 14 wherein the anticoagulant composition further comprises a salt selected from the group consisting of sodium, potassium, and calcium salts.

19. A blood sampling device according to claim 18 wherein the anticoagulant composition comprises a mixture of lithium heparinate and sodium heparinate in a ratio expressed in International Units of from 65:35 to 35:65 as well as a potassium salt.

20. A blood sampling device according to claim 19 wherein the anticoagulant composition comprises a mixture of lithium heparinate and sodium heparinate in a ratio of 50:50 IU as well as a potassium salt.

21. A blood sampling device according to claim 1 wherein the anticoagulant contains lithium as an inactive cation.

22. A blood sampling device according to claim 1 wherein te anticoagulant is solid.

23. A blood sampling device according to claim 1 wherein the receptacle means is in the form of a syringe comprising a syringe cylinder and a piston displaceably arranged therein.

24. A method of treating a blood sample with an anticoagulant, said method comprising passing a predetermined volume of a sample of whole blood into a receptacle, adding to the blood sample within the receptacle a predetermined amount of the anticoagulant, which is capable of binding different cation species in the blood, and adding to the blood sample within the receptacle an additive including selected ones of said different cation species in amounts compensating for proportions of the selected cation species bound by the anticoagulant so as to obtain substantially the same concentration of the selected cation species in an unbound condition in the anticoagulant treated blood sample as in the untreated blood sample.

* * * * *

UNITED STATES PATENT AND TRADEMARK OFFICE
CERTIFICATE OF CORRECTION

PATENT NO. : 4,687,000

DATED : Aug. 18, 1987

INVENTOR(S) : Anne R. Eisenhardt et al.

It is certified that error appears in the above-identified patent and that said Letters Patent is hereby corrected as shown below:

Column 2, line 42: "interantional" should read --international--

Column 5, line 4: "$K^{30}$" should read --$K^+$--

Column 6, line 27: "L vens" should read --Løvens--

Column 6, line 42: "_" should read --$\leq$--

Column 6, line 55: Insert --solution-- between "stock" and "is"

Column 11, line 2: "te" should read --the--

Signed and Sealed this

Twenty-second Day of November, 1988

Attest:

DONALD J. QUIGG

*Attesting Officer*  *Commissioner of Patents and Trademarks*